United States Patent [19]
Vancells

[11] Patent Number: 5,171,894
[45] Date of Patent: Dec. 15, 1992

[54] METHOD FOR PRODUCING STABILIZED SOLUTIONS OF FORMALDEHYDE WITH METHANOL

[75] Inventor: Luis E. Vancells, Barcelona, Spain

[73] Assignee: Patenes y Novedades, Barcelona, Spain

[21] Appl. No.: 613,795

[22] PCT Filed: May 8, 1990

[86] PCT No.: PCT/ES90/00015
§ 371 Date: Jan. 2, 1991
§ 102(e) Date: Jan. 2, 1991

[87] PCT Pub. No.: WO90/13532
PCT Pub. Date: Nov. 15, 1990

[30] Foreign Application Priority Data
May 10, 1989 [ES] Spain .................................. 8901591

[51] Int. Cl.$^5$ ........................ C07C 47/04; C07C 45/85
[52] U.S. Cl. .................................... 568/422; 568/420
[58] Field of Search ............................... 568/422, 420

[56] References Cited
FOREIGN PATENT DOCUMENTS

| 0036362 | 9/1972 | Japan | 568/422 |
| 0073811 | 6/1977 | Japan | 568/422 |
| 0084910 | 7/1978 | Japan | 568/422 |

Primary Examiner—Werren B. Lone
Attorney, Agent, or Firm—Staas & Halsey

[57] ABSTRACT

The method uses a starting material which is a liquid mixture including a formaldehyde proportion between 48 to 55% by weight, a methanol proportion between 20 and 30% by weight and a water proportion between 32 and 15 wt %; the liquid mixture is obtained from a tapping which is effected from a plant for the continuous preparation of urea-formaldehyde resins and glues, immediately after having subjected the methanol to catalytic oxidation via air, condensation of the gases evolving from said catalytic oxidation and separation between condensed products and uncondensed gases. These solutions may be applied to formaldehyde reactions wherein it is of interest to reduce the amount of water present in conventional solutions and also to use the methanol for example as solvent for the final product obtained.

13 Claims, No Drawings

METHOD FOR PRODUCING STABILIZED SOLUTIONS OF FORMALDEHYDE WITH METHANOL

BACKGROUND OF THE INVENTION

1. Field of the Invention

This invention relates to a method for producing stabilized solutions of formaldehyde with methanol.

2. Description of the Related Art

Such solutions are commonly used in reactions of formaldehyde with other products, in which it is of interest to have less water than if a conventional formaldehyde-in-water solution were used and where, furthermore, the presence of methanol is desired, for example, to act as solvent for the end product obtained.

Spanish patent 447,890 discloses a process for the preparation of urea formaldehyde glues and resins, based on the preparation of said glues and or resins from methanol, by preparing a concentrated aqueous formaldehyde solution which is reacted with urea.

The process described in the above patent is characterized by the combination of the following steps:

a) methanol is catalytically oxidized in air;
b) the gases from the catalytic oxidation of the methanol are condensed;
c) the condensates are separated from the uncondensed gases;
d) the uncondensed gases are cooled and washed in a scrubber with a cold polymerized formaldehyde solution which retains the methanol and formaldehyde contained in the gases;
e) the solution obtained in step c) is distilled such that a concentrated aqueous formaldehyde solution and methanol are obtained separately;
f) the solution obtained in step d) is distilled such that the methanol is recovered and the formaldehyde is fixed;
g) a part of the formaldehyde solution obtained in step f) is pooled with the distilled condensate obtained in step e);
h) the concentrated aqueous formaldehyde solution from step e) is mixed with urea under certain pH and temperature conditions to obtain urea-formaldehyde glues or resins.

The above described steps are effected continuously and, in a preferred embodiment, atmospheric air is aspirated at a pressure of 760 mm Hg with an appropriate compressor. The air is blown at a constant flow rate to a saturator and, therein, the air is bubbled through methanol, which is held at 50.5° C. by means of a heating device. In turn, the methanol is supplied to the saturator from a reservoir at a constant rate thanks to an adequate regulation by way of a valve.

Thereafter, the mixture leaving the saturator, also at a constant methanol rate, is fed over a silver metal based catalyst held at a temperature of about 500° C. such that it converts about 60% of the methanol into formaldehyde, in a conventional reaction, the corresponding hydrogen, part of which is oxidized in water by the air oxygen, being released. At the same time, a small amount of carbon dioxide is formed and practically all the air oxygen is converted during the reaction.

The gas mixture from the catalyzer is thereafter fed to the base of a scrubber receiving at the head thereof the condensates removed at the scrubber base, which are circulated by a pump and cooled by a cooler.

In the process of Spanish patent 447,890, the thus collected mixture is fed by a pump through the above mentioned remaining steps up to the preparation of the urea-formaldehyde glues and resins.

SUMMARY OF THE INVENTION

According to the present invention, the mixture cited in the foregoing paragraph forms the starting material for the preparation of said stabilized formaldehyde and methanol solutions. In the Examples given hereinafter, this mixture is referred to as: mixture from the scrubber base.

In other words, the present method is characterized in that the starting material is a liquid mixture comprising a formaldehyde concentration of from 48 to 55 wt %, a methanol concentration of from 20 to 30 wt % and an amount of water of from 32 to 15 wt %, said liquid mixture being tapped from an installation for the continuous preparation of urea-formaldehyde glues and resins, immediately after having subjected the methanol to catalytic oxidation in air, to condensation of the gases from said catalytic oxidation and to separation of the condensates from the uncondensed gases.

According to a further feature of the invention, said liquid mixture is tapped continuously and the liquid mixture is stabilized by the continuous supply of water and a base, using the heat from the liquid mixture itself and from prior heating of said water.

Preferably, according to the invention, the respective flow rates of said continuous supplies may be represented by magnitudes proportional to the following numbers: from 900 to 1100 for said liquid mixture; from 30 to 50 for said hot water and from 1 to 2 for said base.

According to a first embodiment of the invention, said liquid mixture has a composition of 50.5 wt % of formaldehyde, and 26.0 wt % of methanol; said base is triethylamine; the flow rates of the liquid mixture, hot water and triethylamine are in an approximate ratio of 1000:40:1.4, a stabilized solution having a composition of 48.5 wt % of formaldehyde and 25.0% methanol being obtained.

According to another embodiment of the invention, said liquid mixture is tapped batchwise and is stabilized by the addition of water and a base, the mixture being heated to a temperature of from 70° to 100° C. for a time ranging from 5 to 30 minutes; more preferably, said tapped liquid mixture and said water and base additions represent magnitudes proportional to the following numbers: from 12,000 to 15,000 for said liquid mixture; from 500 to 625 for said water and from 15 to 20 for said base.

In an alternative embodiment of the invention, said liquid mixture is tapped continuously and the liquid mixture is stabilized by the continuous supply of a base, followed by continuous low pressure distillation, giving, on the one hand, a concentrate to which methanol is added and, on the other hand, low concentration distillates which may be fed to a dealcoholization column where the methanol and a formaldehyde-containing solution are separated and the respective flow rates of said continuous supplies preferably represent magnitudes proportional to the following numbers: from 900 to 1100 for said liquid mixture and from 1 to 2 for said base and wherein said low pressure ranges from 200 to 300 mm Hg.

In a subsequent embodiment of the invention, said liquid mixture is tapped batchwise and is stabilized with the addition of a base, followed by low pressure distillation, giving, on the one hand, a concentrate to which methanol is added and, on the other hand, low concentration distillates which may be fed to a dealcoholization column where the methanol and a formaldehyde-containing solution are separated, it being a preferred feature that said tapped liquid mixture and said addition of a base represent magnitudes proportional to the following numbers: from 12,000 to 16,000 for said liquid mixture and from 16 to 24 for said base and wherein said low pressure ranges from 160 to 240 mm Hg.

Examples of the invention are given hereinafter without any limiting nature.

EXAMPLE 1

Continuous Preparation of a 48/25 Formaldehyde-Methanol Solution 40 kg per hour of water and 1.4 kg per hour of triethylamine were added by a metering pump system to 1,000 kg per hour of the mixture coming from the base of the scrubber, having a composition of 50.5% of formaldehyde and 26.0% of methanol.

The temperature of the liquid from the base of the scrubber together with the water at 70° C. was used to stabilize the formaldehyde-methanol solution.

The product obtained is stable for a period of over 6 months at 20° C. and has a composition of 48.5% of formaldehyde and 25.0% of methanol.

EXAMPLE 2

Batchwise Preparation of a 48/25 Formaldehyde-Methanol Solution

A reactor equipped with a stirrer and heating and cooling system was charged with a mixture having a composition of 50.5% of formaldehyde and 25% of methanol from the scrubber base. The flow rate was 1,000 kg per hour.

A 14 cu.m. capacity reactor was charged initially with 560 kg of water and 18 kg of 30% caustic soda, whereby 14 tonnes of a solution having a composition 48% of formaldehyde and 25% of methanol was obtained.

The product was stabilized when the reactor charge was complete, by heating to 90° C. for 15 minutes. The product was cooled and drained off.

During the time used for stabilizing the solution, cooling and draining the reactor, the installation described in Spanish patent 447,890 continued running to produce the urea-formaldehyde glues and resins.

EXAMPLE 3

Continuous Preparation of a 55/35 Formaldehyde-Methanol Solution 1.5 kg per hour of 30% caustic soda were added by a metering pump system to 1,000 kg per hour of the mixture coming from the base of the scrubber, having a composition of 50.8% of formaldehyde and 20.0% of methanol and was fed to a continuous distillation or concentration system operating at an absolute pressure of 250 mm Hg. 505 kg per hour of a concentrate having a composition of 74% of formaldehyde and 12.0% of methanol and 495 kg per hour of distillates having a composition of 25.0% of formaldehyde and 28.2% of methanol were obtained, the remainder being water.

These distillates were also continuously fed to a dealcoholization column where the methanol was removed and is recovered for the formaldehyde production system. At the column base formaldehyde with 34.8% methanol was obtained.

179 kg per hour of methanol was supplied continuously to the concentrate resulting from the distillation to adjust the product concentration.

684 kg per hour of a solution containing 54.6% of formaldehyde and 35.0% of methanol were obtained.

EXAMPLE 4

Batchwise Preparation of a 55/35 Formaldehyde-Methanol Solution

A 14 cu.m. capacity reactor equipped with a stirrer and heating, cooling and condenser system and vacuum distilling equipment was charged with a mixture having a composition of 54.8% of formaldehyde and 20.2% of methanol from the scrubber base. The flow rate was 1,000 kg per hour.

When the 14 tonne charge was completed, 20 kg of triethylamine were added and vacuum distillation was effected (absolute pressure 200 mmHg).

The distillation was terminated when the formaldehyde concentration reached 74% and 7,770 kg having a 12% methanol content had been obtained.

2,758 kg of methanol were added and a charge of 10,528 kg having a 54.7% formaldehyde and 35.0% methanol composition was completed. The product obtained was stable for over 6 months at 20° C.

7,639 kg of distillate having a 25% formaldehyde and 25% methanol composition were obtained, the remainder being water. This material was suitably metered by a pump to a dealcoholization column. 5,720 kg of a methanol-free 33.2% formaldehyde solution was obtained, the remainder being water.

During the time used for distilling and stabilizing the solution, cooling and draining the reactor, the installation described in Spanish patent 447,890 continued running to produce the urea-formaldehyde glues and resins.

What I claim is:

1. A method for producing stabilized formaldehyde and methanol solutions, comprising the steps of:
   (a) catalytically oxidizing methanol in air to form formaldehyde;
   (b) condensing gases formed by the catalytic oxidation of methanol;
   (c) separating condensates from uncondensed gases; and
   (d) cooling and washing the uncondensed gases with a cold polymerized formaldehyde solution to form a solution of methanol and formaldehyde;
   (e) stabilizing the solution by continuously supplying water and base, using heat from the liquid mixture and prior heating of the water to yield as a starting material a stable liquid mixture at low temperature including a formaldehyde concentration of from 48 to 55 wt %, a methanol concentration of from 20 to 30 wt % and an amount of water of from 32 to 15 wt % for the continuous preparation of urea-formaldehyde glues and resins.

2. The method of claim 1, wherein the respective flow rates of said continuous supplies represent magnitudes proportional to the following numbers: from 900 to 1100 for said liquid mixture; from 30 to 50 for said hot water and from 1 to 2 for said base.

3. The method of claim 2, wherein said liquid mixture has a composition of 50.5 wt % of formaldehyde, and 26.0 wt of methanol; said base is triethylamine; the flow rates of the liquid mixture, hot water and triethylamine are in an approximate ratio of 1000:40:1.4, there being obtained a stabilized solution having a composition of 48.5 wt % of formaldehyde and 25.0% methanol.

4. The method of claim 1, wherein said liquid mixture is tapped batchwise and is stabilized by the addition of water and a base, the mixture being heated to a temperature of from 70° to 100° C. for a time ranging from 5 to 20 minutes.

5. The method of claim 4, wherein said tapped liquid mixture and said water and base additions represent magnitudes proportional to the following numbers: from 12,000 to 15,000 for said mixture; from 500 to 625 for said water and from 15 to 20 for said base.

6. The method of claim 5, wherein said liquid mixture has a composition of 50.5 wt % of formaldehyde and 25.0% of methanol; said base is 30% caustic soda; and the liquid mixture, water, and caustic soda supplies are in a ratio of 13,422:560:18, there being obtained a stabilized solution having a composition of 48 wt % of formaldehyde and 25 wt % of methanol.

7. The method of claim 1, wherein said liquid mixture is tapped continuously and the liquid mixture is stabilized by the continuous supply of a base, followed by continuous low pressure distillation, giving a concentrate to which methanol is added and low concentration distillates which are fed to a dealcoholization column where the methanol and a formaldehyde-containing solution are separated.

8. The method of claim 7, wherein the respective flow rates of said continuous supplies represent magnitudes proportional to the following numbers: from 900 to 1100 for said liquid mixture and from 1 to 2 for said base and wherein said low pressure ranges from 200 to 300 mm Hg.

9. The method of claim 7, wherein said liquid mixture has a composition of 50.8 wt % of formaldehyde and 20.0 wt % of methanol; said base is 30% caustic soda; and the liquid mixture and caustic soda supply rates are in a ratio of 1000:1.5; the concentrate has a composition of 74 wt % of formaldehyde and 12 wt % of methanol; said methanol being added at a rate, relative to said concentrate, of 505:180, there being obtained a stabilized solution having 55 wt % of formaldehyde and 35 wt % of methanol.

10. The method of claim 1, wherein said liquid mixture is tapped batchwise and is stabilized with the addition of a base, followed by low pressure distillation, giving a concentrate to which methanol is added and low concentration distillates which may be fed to a dealcoholization column where the methanol and a formaldehyde-containing solution are separated.

11. The method of claim 10, wherein liquid mixture tapping and said addition of a base represent magnitudes proportional to the following numbers: from 12,000 to 16,000 for said liquid mixture and from 16 to 24 for said base and wherein said low pressure ranges from 160 to 240 mm Hg.

12. The method of claim 10, wherein said liquid mixture has a composition of 54.8 wt % of formaldehyde and 20.2 wt % of methanol; said base is triethylamine; the liquid mixture and triethylamine supply rates are in a ratio of 14,000:20; the concentrate has a composition of 74 wt % of formaldehyde and 12 wt % of methanol; said methanol being added at a rate, relative to said concentrate, of 1,110:400, there being obtained a stabilized solution having 54.7 wt % of formaldehyde and 35 wt % of methanol.

13. The method of claim 1, wherein said base is selected from the base group consisting of triethylamine and caustic soda.

* * * * *